US011286176B2

(12) United States Patent
Giguere et al.

(10) Patent No.: US 11,286,176 B2
(45) Date of Patent: Mar. 29, 2022

(54) METHODS AND SYSTEM FOR EVALUATING AND MAINTAINING DISINFECTANT LEVELS IN A POTABLE WATER SUPPLY

(71) Applicant: UGSI Solutions, Inc., Poway, CA (US)

(72) Inventors: Robin Giguere, Piedmont, CA (US); Peter Fiske, Oakland, CA (US)

(73) Assignee: UGSI Solutions, Inc., Milpitas, CA (US)

(*) Notice: Subject to any disclaimer, the term of this patent is extended or adjusted under 35 U.S.C. 154(b) by 294 days.

(21) Appl. No.: 16/310,671

(22) PCT Filed: Jun. 30, 2017

(86) PCT No.: PCT/US2017/040263
§ 371 (c)(1),
(2) Date: Dec. 17, 2018

(87) PCT Pub. No.: WO2018/005952
PCT Pub. Date: Jan. 4, 2018

(65) Prior Publication Data
US 2019/0194034 A1 Jun. 27, 2019

Related U.S. Application Data

(60) Provisional application No. 62/356,718, filed on Jun. 30, 2016.

(51) Int. Cl.
C02F 1/00 (2006.01)
C02F 1/76 (2006.01)
(Continued)

(52) U.S. Cl.
CPC .............. C02F 1/008 (2013.01); C02F 1/766 (2013.01); G01N 27/4168 (2013.01);
(Continued)

(58) Field of Classification Search
CPC .. C02F 1/008; C02F 1/766; C02F 1/76; C02F 1/00; C02F 2209/003; C02F 2209/005;
(Continued)

(56) References Cited

U.S. PATENT DOCUMENTS 4,406,582 A 9/1983 LaGrange
4,435,291 A 3/1984 Matsko
(Continued)

FOREIGN PATENT DOCUMENTS

WO 0238507 A1 5/2002
WO 2009055093 A1 4/2009
(Continued)

OTHER PUBLICATIONS

Yu et al., Mar. 2003, "Determination of chlorine demand in water and wastewater chlorination by oxidation-reduction potential", pp. 313-320.*
(Continued)

Primary Examiner — Akash K Varma
(74) Attorney, Agent, or Firm — The Webb Law Firm

(57) ABSTRACT

A method of determining a disinfectant composition of a municipal water supply from a water sample that includes: (a) obtaining a water sample from a water source at a sampling location; (b) adding a chlorine-containing material to the water sample in the presence of an oxidation reduction potential (ORP) measurement device; (c) generating a plurality of ORP measurements during addition of the chlorine-containing material to the water sample; (d) estimating a concentration of one or more of free ammonia, fully combined ammonia, monochloramine, or a mixture of dichloramine and trichloramine in the water sample in which the estimation is derived from the relationship between the added chlorine material and the plurality of ORP measurements; and (e) determining a disinfectant composition of the
(Continued)

water source at the water sampling location from the concentration calculation. A method of determining free ammonia composition is also included.

17 Claims, 2 Drawing Sheets

(51) Int. Cl.
G01N 27/416 (2006.01)
G01N 33/18 (2006.01)
(52) U.S. Cl.
CPC ............ *G01N 33/188* (2013.01); *C02F 1/76* (2013.01); *C02F 2209/003* (2013.01); *C02F 2209/005* (2013.01); *C02F 2209/02* (2013.01); *C02F 2209/04* (2013.01); *C02F 2209/06* (2013.01); *C02F 2209/14* (2013.01)
(58) Field of Classification Search
CPC ............ C02F 2209/02; C02F 2209/04; C02F 2209/06; C02F 2209/14; C02F 2209/29; C02F 9/00; C02F 2303/04; G01N 27/4168; G01N 27/416; G01N 33/188; G01N 33/18; Y10T 436/193333; Y10T 436/175383
USPC ........................................................ 210/96.1
See application file for complete search history.

(56) References Cited

U.S. PATENT DOCUMENTS

| | | | |
|---|---|---|---|
| 4,752,740 A | 6/1988 | Steininger |
| 5,547,584 A | 8/1996 | Capehart |
| 5,854,744 A | 12/1998 | Zeng et al. |
| 5,934,877 A | 8/1999 | Harman |
| 6,143,184 A | 11/2000 | Martin et al. |
| 6,315,950 B1 | 11/2001 | Harp et al. |
| 6,702,551 B2 | 3/2004 | Kikuchi et al. |
| 6,702,552 B1 | 3/2004 | Harman |
| 6,716,354 B2 | 4/2004 | Rosenblatt et al. |
| 7,300,592 B2 | 11/2007 | Iseki et al. |
| 7,488,151 B2 | 2/2009 | Harman |
| 7,862,302 B2 | 1/2011 | Harman |
| 8,051,383 B2 | 11/2011 | McCampbell et al. |
| 8,887,556 B2 | 11/2014 | Silveri |
| 9,039,902 B2 | 5/2015 | Simmons et al. |
| 2003/0232447 A1* | 12/2003 | Kahle ................. G01N 33/182 |
| | | | 436/113 |
| 2005/0137118 A1 | 6/2005 | Silveri |
| 2006/0096930 A1 | 5/2006 | Beardwood |
| 2006/0124558 A1 | 6/2006 | Kouame |
| 2006/0131245 A1 | 6/2006 | Dennis, II et al. |
| 2009/0320570 A1 | 12/2009 | Wiese |
| 2011/0210078 A1 | 9/2011 | Simmons et al. |
| 2012/0021062 A1 | 1/2012 | Gupta et al. |
| 2015/0203388 A1 | 7/2015 | Gotthardt et al. |
| 2015/0329391 A1 | 11/2015 | Garusi et al. |
| 2016/0362318 A1 | 12/2016 | Simmons |
| 2016/0376166 A1 | 12/2016 | Lawryshyn et al. |
| 2017/0190601 A1 | 7/2017 | Augustine et al. |
| 2017/0203974 A1 | 7/2017 | Riedl et al. |
| 2017/0253502 A1 | 9/2017 | Bejan et al. |
| 2018/0282882 A1 | 10/2018 | Boal et al. |
| 2018/0346358 A1 | 12/2018 | Fritz et al. |
| 2019/0084849 A1 | 3/2019 | Giguere |

FOREIGN PATENT DOCUMENTS

| | | |
|---|---|---|
| WO | 2012010864 A1 | 1/2012 |
| WO | 2013009106 A2 | 1/2013 |
| WO | 2015179919 A1 | 12/2015 |
| WO | 2015187982 A1 | 12/2015 |

OTHER PUBLICATIONS

Baribeau, "Nitrification in Distribution Systems: Effects, Cause, and Control", AWWA 2015 Operator Symposium, 2015, AQUAlity Engineering, Inc., Ontario, California.
Turner, "Slope Filtering: An FIR Approach to Linear Regression", IEEE Signal Processing Magazine, Nov. 2008, pp. 159-163.
"Chemistry of Aqueous Chlorine", White's Handbook of Chlorination and Alternative Disinfectants, 2010, pp. 102-117, 5th Edition.
Steininger, "PPM or ORP: Which Should Be Used?", Swimming Pool Age & Spa Merchandiser, Nov. 1985.
Yu et al., "Determination of chlorine demand in water and wastewater chlorination by oxidation-reduction potential", Water Science and Technology: Water Supply, 2003, pp. 313-320, vol. 3, No. 1-2.
"Oxidation Reduction Potential (ORP)/Redox and Free Chlorine", Myron L Company, 2012.
Demir, et al., Feedback control over the chlorine disinfection process at a wastewater treatment plant using a Smith predictor, a method of characteristics and odometric transformation, J Env Chem Engg, 2 (2014) 1088-1097 (Year: 2014).

* cited by examiner

METHODS AND SYSTEM FOR EVALUATING AND MAINTAINING DISINFECTANT LEVELS IN A POTABLE WATER SUPPLY

CROSS-REFERENCE TO RELATED APPLICATIONS

This application is the United States national phase of International Application No. PCT/US2017/040263 filed Jun. 30, 2017, and claims the benefit of U.S. Provisional Patent Application No. 62/356,718 filed Jun. 30, 2016, each of which is incorporated herein by reference in its entirety.

BACKGROUND OF THE INVENTION

Field of the Invention

The present invention relates to methods and devices for evaluating the disinfectant composition of a potable water supply and, in particular, methods of determining the presence of and estimation of the amounts of one or more of free ammonia, mono-, di- or tri-chloramines therein as well as systems for measuring and maintaining the chloramination and free ammonia levels of a potable water supply.

Description of Related Art

Water used for human or animal consumption must be treated to remove pathogens and contaminants. After treatment, a "residual disinfectant" is usually applied to the water to prevent the regrowth of pathogens. This is also termed "secondary disinfection." In municipal water systems, chlorine or chloramines (monochloramine: $NH_2Cl$) are typically used for this purpose. Many municipal water systems in the United States and abroad increasingly use chloramines, which are chemically more stable and less reactive, and, thus, can persist longer in the distribution system.

With the increased use of chloramines as a strategy to reduce disinfection byproduct levels in the municipal water supplies, in particular those used to deliver potable water to consumers, enhanced analysis and treatment techniques are needed. Municipal water systems are mandated by mission, as well as regulatory regimes, to ensure that water remains safe for human consumption, not only at the treatment plant location, but at all locations in the delivery system, including at or near the faucet where the water is finally delivered to the consumer. Competing with the demand for safety is the need to reduce off-tasting materials in the water, which, while not necessarily unsafe, can result in consumer perception that the water is unsanitary. As an additional issue, managers of water supplies must endeavor to treat water using the most cost-effective methods available, which means that accurate measurement of required chemical levels and process controls for delivering those chemicals are required to ensure that money is not wasted.

Chloramine chemistry has been described for some time, especially in regard to wastewater treatment and the disinfection of water cooling towers used in air conditioning systems. In these applications, the goal generally is to reduce the amount of biological contaminants present in order to also reduce the possibility of humans or other biological systems from becoming ill from such contamination.

Maintaining proper chloramine chemistry throughout a water distribution network is difficult. At least some free ammonia is typically maintained in water systems—generally less than about 0.1 mg/L—to better ensure that chloramination remains effective throughout a water distribution network. Because the chlorine in the molecule reacts with organic matter in the water, some amount of chlorine will be deactivated from use as a disinfectant. As a result, with time, the water can accumulate excess free ammonia. For other water sources that may be used as potable water, such as wells, free ammonia may be natively present in the water due to biological and water source artifacts. The presence of free ammonia greatly increases the risk of nitrification—a microbial process that converts ammonia to nitrite and then nitrate. Elevated levels of nitrate can make the water unfit for human consumption. Nitrification is a common occurrence in chloraminated potable water systems. Accordingly, water system operators spend large amounts of time attempting to prevent or mitigate nitrification, mainly by closely monitoring and managing free ammonia levels in the water supply.

Chloraminated water systems must be carefully monitored at multiple points in a water distribution network to appropriately detect the onset of nitrification and portions of the water system are flushed to remove water with low disinfectant residual or elevated nitrite levels. Flushing not only wastes water and resources, the process is time consuming and can disrupt water supplies.

Many existing analysis and water treatment methods for use with chloramine disinfection do not contemplate that the chloramine treated water will be ingested by a human or will otherwise be used to provide hydration to a biological system. Moreover, water may test as within appropriate limits at a treatment plant, but as the water travels though the water system, the chloramination level can change markedly, resulting in water that is either not adequately disinfected by the time it exits the faucet of a consumer, or that exhibits an off-taste due to the presence of di- or trichloramines.

Standard methods to measure monochloramine only are available. The monochloramine can be determined amperometrically or titrated with ferrous ammonium sulfate (FAS) using a colorimetric DPD (N,N Diethyl-1,4 Phenylenediamine Sulfate) indicator under controlled conditions. These methods are best used in a lab situation and require a higher degree of skill and care to perform the analysis. Both methods require good control of the reagents added to limit dichloramine interference and can also have interference from organic chloramines. Accordingly, these standard methodologies are generally not suitable to ongoing measurement within a municipal water delivery system, especially in regard to obtaining real time measurements of potable water that is in the process of being delivered to consumers.

Ammonia detection is also relevant in a municipal water distribution system. Because the presence of excess free ammonia greatly increases the risk of nitrification, efforts must be made to minimize free ammonia levels in chloraminated potable water systems. Free ammonia levels can be measured with a variety of field and laboratory methods. However, many of the field techniques have reliability issues at the low concentrations that occur in properly functioning potable water systems, for example, generally below 0.1 mg/l.

In this regard, one secondary disinfectant control strategy uses a very small (ppb) free ammonia concentration to ensure that monochloramine is the predominant species, with the goal to provide secondary disinfection without creating the foul tasting di- and trichloraminated species. If the free ammonia concentration is kept very low, the potential of nitrifying bacteria developing in the distribution system is minimized. However, in practicality, the control of free ammonia at the low ppm range, especially in the water distribution environment, is difficult because of other variables that affect the ability to accurately and closely monitor such a low level of free ammonia in a large volume of water, especially when adding ammonia precisely to a large volume while still managing chlorine levels to remain within specification. If too much ammonia containing material is added, more chlorine will have to be added, otherwise excess of ammonia will be present as a food source for the nitrification process. If too much chlorine containing material is added, di- or trichloramines can be created, and free ammonia will have to be back added to reset the levels to 5:1 (by weight) or to 1:1 (by stoichiometry) required for monochloramine speciation. Alternatively, the systems will need be flushed, as discussed earlier.

Moreover, existing free ammonia analysis requires reagents that are cumbersome to deploy in field settings. The complexity of free ammonia testing, coupled with the high stakes involved in ensuring safe potable water for consumers, generally requires highly trained personnel to conduct the testing, a reality that further limits deployment of free ammonia analysis in the field. In short, today there is no free ammonia test methodology that can provide truly accurate results when the test is conducted outside of a laboratory. As a result of these deficiencies in analysis techniques, water system operators have a difficult time in optimizing and maintaining chloramine chemistry in potable water systems, thus leaving water systems vulnerable to nitrification and/or over-chlorination or both.

Oxidation reduction potential (ORP) has been used to measure chlorine (and other oxidant) levels in water. Measurements of ORP in water can reflect the ability of certain chemical components in the water to accept or lose electrons. In laboratory settings where ongoing electrode calibration and process controls are available, ORP can exhibit high reliability. However, they are not used for analysis and treatment of municipal water supplies or well water because of inaccuracies inherent in the measurements that can result from at least pH, temperature, and water source effects (e.g., metals, $CaCO_3$, etc., that are present as a function of the location where the water is sourced and/or the path it travels during delivery to the consumer). The ORP electrodes themselves are highly sensitive to deposits that affect ORP measurement kinetics and require frequent maintenance to remove buildup that occurs on the electrode surface. While pH, temperature, dissolved materials and electrode deposit effects that may affect ORP measurements can be readily addressed in laboratory settings to enable the method to provide accurate chlorination information, ORP cannot readily be deployed in field settings for the measurement and management of chloramination disinfection of municipal water supplies, especially in relation to estimation of the amount of free ammonia present in a water supply. Put simply, ORP is not seen to be reliable in indicating chloramination levels in water systems. Therefore, this methodology is not deployed by health departments to evaluate safe disinfectant levels.

There remains a need for methods to better measure and manage disinfectant composition in municipal water supplies at locations downstream from water treatment facilities or in wells. Methodologies to measure and manage chloraminated speciation and free ammonia levels to a more controlled degree are also needed. There is also need for methods that can be deployed by technicians without sophisticated chemical training and skills or that can be deployed inline using automated processes.

SUMMARY OF THE INVENTION

In certain non-limiting embodiments, the present invention is directed to a method of determining a disinfectant composition of a municipal water supply from a water sample that includes: (a) obtaining a water sample from a water source at a sampling location; (b) adding a chlorine-containing material to the water sample in the presence of an oxidation reduction potential (ORP) measurement device; (c) generating a plurality of ORP measurements during addition of the chlorine-containing material to the water sample; (d) estimating a concentration of one or more of free ammonia, fully combined ammonia, monochloramine, or a mixture of dichloramine and trichloramine in the water sample from which the estimation is derived based on the relationship between the added chlorine material and the plurality of ORP measurements; and (e) determining a disinfectant composition of the water source at the water sampling location from the concentration calculation. Further, as to the step of obtaining a water sample: (i) the water sample is derived from a water treatment facility; (ii) a chlorine-containing material and an ammonia-containing material are present in the water source; and (iii) the sampling location is located downstream from the water treatment facility.

In some non-limiting embodiments, the concentration is estimated by monitoring the rate of change of ORP measurement in millivolts as a function of the amount of chlorine-containing material added to the water sample. In addition, the concentration can also be estimated by calculating a slope obtained by plotting the ORP of the water sample versus the amount of chlorine-containing material added to the water sample. Moreover, the disinfectant composition is determined as a real-time measurement.

In certain non-limiting embodiments, the chlorine-containing material is added to the water sample in a known volume while generating the plurality of ORP measurements to determine the relationship between the added chlorine material and the plurality of ORP measurements. In some non-limiting embodiments, the method further includes comparing the plurality of ORP measurements obtained from the water sample located downstream from the water treatment facility to ORP measurements obtained from a water sample obtained at the water treatment facility to determine disinfection efficacy. In certain non-limiting embodiments, the estimation provides the concentration of both free ammonia and monochloramine in the water sample.

In some non-limiting embodiments, the method further includes, after determining the disinfectant composition of the water source, adding additional chlorine-containing materials and ammonia containing materials to the water source to achieve a desired level of the disinfectant composition. Moreover, an amount of the added additional chlorine-containing materials and ammonia-containing materials can be independent of a concentration of the chlorine-containing materials and ammonia-containing materials. In addition, in some non-limiting embodiments, a volume of the water sample obtained from the water source is known.

In certain non-limiting embodiments, the present invention is directed to a method of determining a free ammonia composition of a water supply. The method includes: (a) obtaining a water sample from a water supply at a sampling location; (b) adding a chlorine-containing material to the water sample in the presence of an oxidation reduction potential (ORP) measurement device; (c) generating a plurality of ORP measurements during addition of the chlorine-containing material to the water sample; and (d) estimating a concentration of free ammonia in the water sample in which the estimation is derived from the relationship between the added chlorine material and the plurality of ORP measurements.

In some non-limiting embodiments, the method also includes maintaining a concentration of free ammonia in the water supply within a range of greater than 0 mg/L and less than about 0.1 mg/L. In addition, in certain non-limiting embodiments, the water sample is derived from a water treatment facility and the sampling location is located downstream from the water treatment facility. The method of determining free ammonia composition can also be substantially free of a reagent other than chlorine and ammonia-containing materials.

In some non-limiting embodiments, the concentration of free ammonia is estimated from monitoring the rate of change of ORP measurement in millivolts as a function of the amount of chlorine-containing material added to the water sample. Further, in some non-limiting embodiments, the method further includes adding additional chlorine-containing materials when the estimated ammonia concentration is above a desired ammonia concentration range.

In certain non-limiting embodiments, the present invention is directed to a system for maintaining the disinfectant level of a potable water supply. The system can include: (a) a water quality assessment module that includes (i) a plurality of sensors comprising at least an oxidation reduction potential sensor (ORP), and (ii) a control module in operational engagement with the plurality of sensors; (b) a water supply intended for delivery of potable water to a consumer; (c) a water sampling device comprising a fluid delivery means configured to provide a sample of water derived from the water supply to the water quality assessment module; and (d) a chlorine feed source and an ammonia feed source in which each of the sources are, independently: (i) in operational engagement with the water quality assessment module; and (ii) in fluid communication with the water supply. Further, the system is configured to measure and adjust the chloramination level and the free ammonia levels of a portable water supply prior to delivery of the water supply to the consumer.

In some non-limiting embodiments, the water quality assessment module is configured to provide information regarding at least a disinfectant level of the water supply. Further, the water supply can be maintained in a water storage tank. In certain non-limiting embodiments, the water storage tank includes a mixing module.

In certain non-limiting embodiments, the water sampling device further includes a pump. In addition, in some non-limiting embodiments, a volume of the sample of water provided by the delivery means is known. The plurality of sensors used with the system can also include a pH sensor and a temperature sensor.

The present invention is also directed to the following clauses:

Clause 1: A method of determining a disinfectant composition of a municipal water supply from a water sample comprising: (a) obtaining a water sample from a water source at a sampling location, wherein: (i) the water sample is derived from a water treatment facility; (ii) a chlorine-containing material and an ammonia-containing material are present in the water source; and (iii) the sampling location is located downstream from the water treatment facility; (b) adding a chlorine-containing material to the water sample in the presence of an oxidation reduction potential (ORP) measurement device; (c) generating a plurality of ORP measurements during addition of the chlorine-containing material to the water sample; (d) estimating a concentration of one or more of free ammonia, fully combined ammonia, monochloramine, or a mixture of dichloramine and trichloramine in the water sample, wherein the determination is derived from the relationship between the added chlorine material and the plurality of ORP measurements; and (e) determining a disinfectant composition of the water source at the water sampling location from the concentration calculation.

Clause 2: The method of clause 1, wherein the concentration is estimated from monitoring the rate of change of ORP measurement in millivolts as a function of the amount of chlorine-containing material added to the water sample.

Clause 3: The method of clauses 1 or 2, wherein the concentration is determined by calculating a slope obtained by plotting the ORP of the water sample versus the amount of chlorine-containing material added to the water sample.

Clause 4: The method of any of clauses 1 to 3, wherein the disinfectant composition is determined as a real-time measurement.

Clause 5: The method of any of clauses 1 to 4, wherein the chlorine-containing material is added to the water sample in a known volume while generating the plurality of ORP measurements to determine the relationship between the added chlorine material and the plurality of ORP measurements.

Clause 6: The method of any of clauses 1 to 5, further comprising comparing the plurality of ORP measurements obtained from the water sample located downstream from the water treatment facility to ORP measurements obtained from a water sample obtained at the water treatment facility to determine disinfection efficacy.

Clause 7: The method of any of clauses 1 to 6, wherein the estimation provides the concentration of both free ammonia and monochloramine in the water sample.

Clause 8: The method of any of clauses 1 to 7, further comprising, after determining the disinfectant composition of the water source, adding additional chlorine-containing materials and ammonia-containing materials to the water source to achieve a desired level of the disinfectant composition.

Clause 9: The method of clause 8, wherein an amount of the added additional chlorine-containing materials and ammonia-containing materials is independent of a concentration of the chlorine-containing materials and ammonia-containing materials.

Clause 10: The method of any of clauses 1 to 9, wherein a volume of the water sample obtained from the water source is known.

Clause 11: A method of determining free ammonia composition of a water supply comprising: (a) obtaining a water sample from a water supply at a sampling location; (b) adding a chlorine-containing material to the water sample in the presence of an oxidation reduction potential (ORP) measurement device; (c) generating a plurality of ORP measurements during addition of the chlorine-containing material to the water sample; and (d) estimating a concentration of free ammonia in the water sample, wherein the estimation is derived from the relationship between the added chlorine material and the plurality of ORP measurements.

Clause 12: The method of clause 11, wherein a volume of the water sample obtained from the water source is known.

Clause 13: The method of clauses 11 or 12, wherein the water is derived from a water treatment facility and the sampling location is located downstream from the water treatment facility.

Clause 14: The method of any of clauses 11 to 13, further comprising maintaining a concentration of free ammonia in the water supply within a range of greater than 0 mg/L and less than about 0.1 mg/L.

Clause 15: The method of any of clauses 11 to 14, wherein the method of determining free ammonia composition is substantially free of a reagent other than chlorine and ammonia-containing materials.

Clause 16: The method of any of clauses 11 to 15, wherein the concentration of free ammonia is estimated by monitoring the rate of change of ORP measurement in millivolts as a function of the amount of chlorine-containing material added to the water sample.

Clause 17: The method of any of clauses 11 to 16, further comprising adding chlorine-containing materials when the estimated ammonia concentration is above a desired ammonia concentration range.

Clause 18: A system for maintaining the disinfectant level of a potable water supply comprising: (a) a water quality assessment module comprising: (i) a plurality of sensors comprising at least an oxidation reduction potential sensor (ORP); and (ii) a control module in operational engagement with the plurality of sensors; (b) a water supply intended for delivery of potable water to a consumer; (c) a water sampling device comprising a fluid delivery means configured to provide a sample of water derived from the water supply to the water quality assessment module; (d) a chlorine feed source and an ammonia feed source, wherein each of the sources are, independently: (i) in operational engagement with the water quality assessment module; and (ii) in fluid communication with the water supply, wherein the system is configured to measure and adjust the chloramination level and the free ammonia levels of a potable water supply prior to delivery of the water supply to the consumer.

Clause 19: The system of clause 18, wherein the water quality assessment module is configured to provide information regarding at least a disinfectant level of the water supply.

Clause 20: The system of clause 19, wherein the water supply is maintained in a water storage tank.

Clause 21: The system of clause 20, wherein the water storage tank includes a mixing module.

Clause 22: The system of any of clauses 18 to 21, wherein the water sampling device further comprises a pump.

Clause 23: The system of any of clauses 18 to 22, wherein the volume of the sample of water provided by the delivery means is known.

Clause 24: The system of any of clauses 18 to 23, wherein the plurality of sensors further comprise a pH sensor and a temperature sensor.

DESCRIPTION OF THE INVENTION

Figure 1:
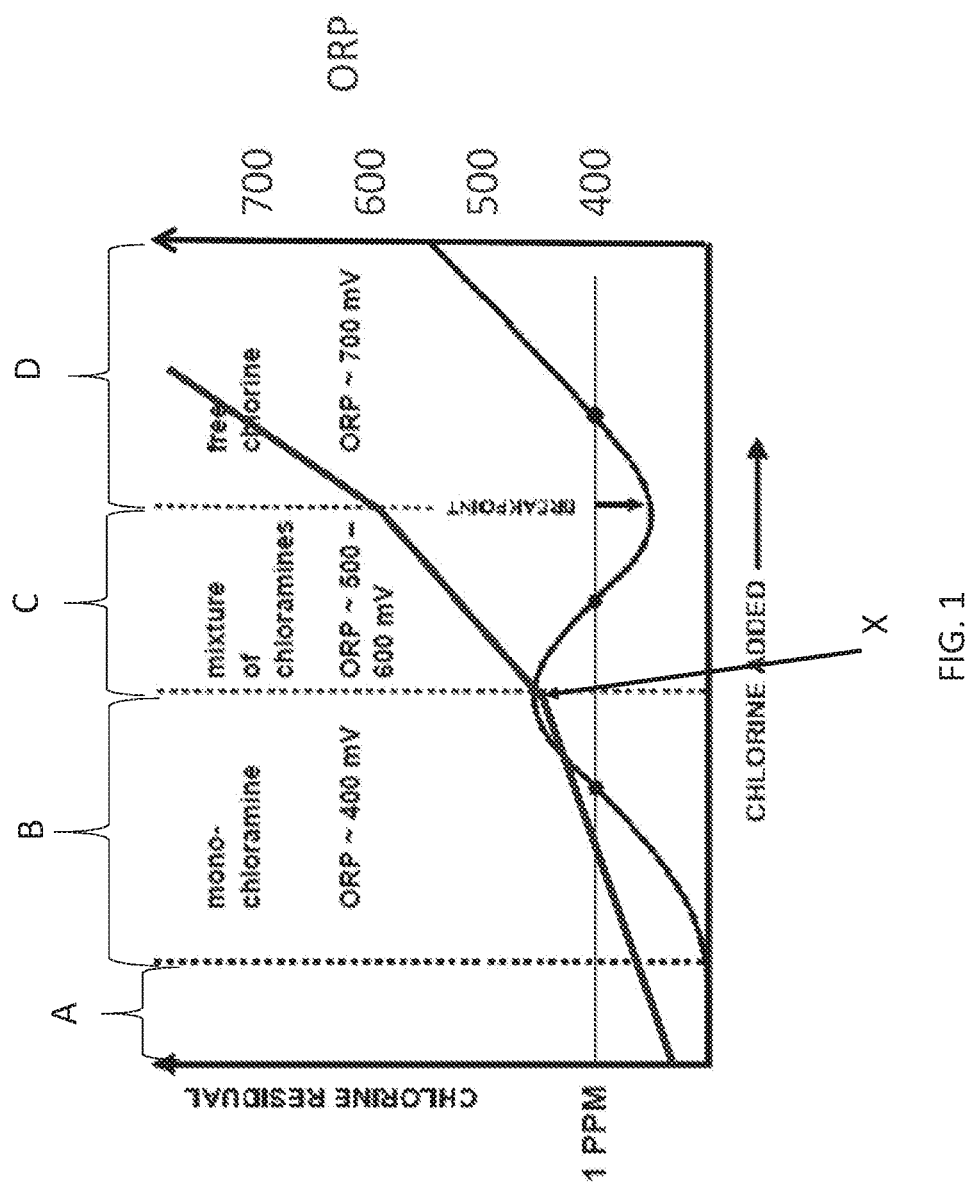
FIG. 1 illustrates a method of determining disinfectant composition of potable water by measurement of ORP.

In the following detailed description, reference is made to the accompanying drawings, which form a part hereof, and within which are shown by way of illustration certain embodiments by which the subject matter of this disclosure may be practiced. It is to be understood that other embodiments may be utilized and structural changes may be made without departing from the scope of the disclosure. In other words, illustrative embodiments and aspects are described below. It will, of course, be appreciated that in the development of any such actual embodiment, numerous implementation-specific decisions must be made to achieve the developers' specific goals, such as compliance with system-related and business-related constraints, which may vary from one implementation to another. Moreover, it will be appreciated that such development effort might be complex and time consuming, but would nevertheless be a routine undertaking for those of ordinary skill in the art having the benefit of this disclosure.

Unless defined otherwise, all technical and scientific terms used herein have the same meaning as is commonly understood by one of ordinary skill in the art to which this disclosure belongs. In the event that there is a plurality of definitions for a term herein, those in this section prevail unless stated otherwise.

Wherever the phrases "for example," "such as," "including," and the like are used herein, the phrase "and without limitation" is understood to follow unless explicitly stated otherwise.

The terms "comprising" and "including" and "involving" (and similarly "comprises" and "includes" and "involves") are used interchangeably and mean the same thing. Specifically, each of the terms is defined consistent with the common United States patent law definition of "comprising" and is therefore interpreted to be an open term meaning "at least the following" and is also interpreted not to exclude additional features, limitations, aspects, etc.

The term "about" is meant to account for variations due to experimental error. All measurements or numbers are implicitly understood to be modified by the word about, even if the measurement or number is not explicitly modified by the word about.

The term "substantially" (or alternatively "effectively") is meant to permit deviations from the descriptive term that do not negatively impact the intended purpose. Descriptive terms are implicitly understood to be modified by the word substantially, even if the term is not explicitly modified by the word substantially.

"Water supply" as used herein means water generated from a municipal water supply, a well system or both.

The term "disinfectant composition" comprises the amounts of one or more of free ammonia, fully-combined ammonia, monochloramine, dichloramine, trichloramine, or free chlorine that is present in the water supply. Disinfection composition can be estimated from a water sample derived from the water supply as discussed elsewhere herein.

The term "municipal water supply" means a water supply provided from a central point and piped to individual users under pressure. Water sources used to generate municipal water supplies can vary. As required by regulations, municipal water supplies will undergo primary disinfection to make it suitable for use as potable water at the treatment facility. Secondary disinfection with chloramination processes will also be provided at the water treatment plant to ensure that the water will remain suitable for use as potable water as it travels through the water system to the consumer.

"Well water" is water obtained from a below-ground water source such as an aquifer, and that is stored (or storable) for supply as potable water, among other uses. As would be recognized, well water can natively comprise free ammonia as a result of natural processes. Well water may or may not be disinfected prior to use.

In certain non-limiting embodiments, the present invention comprises a method of determining disinfectant compositions in potable water at locations in a municipal potable water supply that are located downstream from a water treatment facility. In this regard, the present invention relates to maintaining adequate secondary disinfection of a potable water supply, where "secondary disinfection" means the maintenance of free or combined chlorine levels in a water supply once the water is treated with primary disinfecting methods (e.g., sedimentation, coagulation, UV, chlorine gas, etc.). Yet further, the present invention relates to systems in which the disinfectant level determination can be implemented.

As would be recognized, "primary disinfectants" are intended to kill or otherwise deactivate pathogens that exist in a water source upon its arrival at a treatment plant, whereas "secondary disinfectants" are intended to maintain the healthiness and cleanliness of the water supply upon leaving the treatment plant throughout its path through a municipal water system until it reaches the faucet of a consumer.

The present invention relates, in some non-limiting embodiments, to estimating, maintaining, and adjusting the secondary disinfectant composition of potable water supplies where the secondary disinfection is provided in part or in full by way of chloramines. Disinfection composition is estimated and/or maintained by measuring the presence (or lack thereof) of a disinfecting species of interest using an ORP electrode as discussed elsewhere herein. In this regard, at the water treatment plant, for secondary disinfection, chlorine or a chlorine-containing material will be added to the water supply. Ammonia or ammonia-containing materials will also be added to the water supply during treatment, usually after addition of the chlorine-containing material, when secondary disinfection is to be effected and maintained by chloramination, as in the present invention. Note that, while ammonia is generally added to water supplies to provide suitable secondary disinfection with chloramines, some ammonia-containing materials may be naturally present in the water source when it reaches the treatment facility. Such naturally occurring ammonia material, which will vary from water source to water source, will be included in the discussions related to free ammonia detection herein.

During one or more periods in the water distribution timeline and/or at one or more locations in the water distribution network, the amount of one or more of the disinfectant compositions of interest can be estimated by measuring the ORP of the sample during addition of chlorine (or a chlorine containing material) to the water sample. The amount of disinfectant composition of interest in the water sample can then be estimated from one or more of previously identified dose response curves, as discussed further herein.

In some non-limiting embodiments, the present invention relates to devices and methods to estimate the free ammonia concentration in a water supply by extrapolating concentrations estimated from a water sample obtained from the water supply. The free ammonia estimation can be generated after the water leaves a water treatment facility and prior to delivery of the water to a consumer, where the sampling is taken at one or more locations in the water distribution network and/or at different times. The present invention allows a water supply to be sampled and tested for free ammonia levels using simple and reliable testing methodologies, in particular, ORP measurement of a water sample derived from the water supply of interest. The ammonia estimation of the present invention can also be conducted on water that has not previously been treated in a primary disinfectant regime, such as water sourced from or otherwise present in a well, where free ammonia may be natively present therein.

ORP can be used to determine or estimate the levels of chemical disinfectants that work via the oxidation or reduction of the structures of microbial contaminants. For example, chlorine, an oxidant, will strip electrons from the negatively charged cell walls of some bacteria, thus rendering it harmless to the potable water consumer. The inventors have found that because ORP suitably measures the total chemical activity of a solution—which in the present invention correlates to a disinfecting species composition—ORP as described herein can estimate the total composition of all, or substantially all, oxidizing and reducing disinfectants in solution. While in the case of the present invention, the level of chloramines (e.g., mono-, di- and tri-) are of primary relevance, other oxidants that may be used in water to act in a redox capacity to inactivate harmful materials in water are also analyzable according to the ORP methods and devices herein: hypochlorous acid, sodium hypochlorite, UV, ozone, peracetic acid, bromochlorodimethylhydantoin, etc.

When other factors in a water sample are substantially stable (temperature, pH, etc.), ORP values are related to disinfectant composition in a water sample and, therefore, the water supply from which the sample is derived. As the concentration of chlorine-containing material, for example, chloramine species, in a water sample changes, the ORP value changes. Accordingly, ORP has been found to provide a reliable estimation of disinfectant composition in a water sample that has been subjected to a chloramination disinfection methodology.

In some non-limiting embodiments the present invention substantially characterizes a disinfectant composition in a water sample, as opposed to being a direct detection method of a particular chemical or chemical species. That is, ORP indicates the effectiveness of those disinfectant materials that work through oxidation and reduction. Use of this method by itself cannot generally determine the exact concentrations of known species of chemical in solution without collection of additional information. However, when applied to test previously treated municipal water supplies, the regulatory regimes applicable to municipal water supplies greatly restrict the types and amounts of chemicals and chemical species that may be present in potable water. Moreover, since, in some non-limiting embodiments, the water samples evaluated herein are derived from water supplies emanating from water treatment facilities, any ORP measurements can be used to not only estimate the disinfecting composition of a water sample, and, thus, the municipal water supply itself at the point of testing, but also to confirm the type and amount of a sanitizing chemical that is providing the secondary disinfection to the potable water in real time.

The present invention can also be used to estimate the free ammonia concentration of untreated water, such as well water. In this regard, chlorine (or chlorine-containing material) is added to a water sample obtained from a water supply and the dose response curve is used to generate a concentration estimation.

The present invention allows ORP to be deployed to test secondary disinfection species composition in municipal water supplies to obtain real time, online measurements. Such real time, online measurements represent a substantial advance in the management of municipal potable water supply systems. That is, water systems operators have historically been challenged to guarantee to potable water consumers that potable water maintains its safety once it leaves the water treatment facility.

The complexities required to obtain accurate analysis of water has generally required samples to be taken from water sources for analysis under laboratory conditions. Such complexities are exacerbated by the small quantities of materials that must be quantified to ensure that potable water is safe and complies with the extensive regulatory regimes. The present invention greatly simplifies the analysis, and, therefore, provides heretofore unavailable economies and ease of deployment in the field to provide "just in time" knowledge about the disinfectant composition of a municipal water supply as the water travels through the distribution network from the water treatment plant to the consumer. Still further, the present invention enables the automated optimization of chloramine disinfectant composition and concentration in the water distribution system, where such automation is discussed elsewhere herein. Yet further, the present invention provides an improved methodology to estimate free ammonia composition in water supplies, where such knowledge is of interest in determining nitrification potential of the water supply from which the water sample is derived.

As used herein, "substantially accurate estimation of disinfectant composition in potable water" means the ability to distinguish between potable water with excess free ammonia and potable water with excess di- or trichloramine species, as well as free chlorine, if the system has moved past the chlorine breakpoint, as such materials and terms are known to those of ordinary skill in the art.

Still further, the present invention provides a previously unavailable methodology to enable water supply operators to maintain the secondary disinfection regime substantially at all times in the water delivery network in the monochloramine species part of the speciation curve. (See FIG. 1). Yet further, the present invention allows substantially precise control of the monochloramine disinfectant regime so as to allow the amount of free ammonia in a potable water supply to be maintained within the desired range of from greater than 0 mg/L to less than about 0.1 mg/L, where such range is the optimum for managing chloraminated systems. In short, the present invention provides effective chloramination disinfection while still reducing the potential for the chloraminated water supply to undergo nitrification, as discussed hereinafter.

In use, a technician can manually obtain a sample of water from a location downstream of the water treatment facility, that is, after the water has undergone primary disinfection and is in the process of being delivered to consumers for use. Alternatively, an automatic inline process can be used to sample the potable water after it leaves the treatment facility. The locations where the water can be sampled for disinfectant composition are expansive, however, it may generally be more suitable to test in locations where the water collects for storage or is otherwise staged for delivery. In this regard, if it is determined that the potable water is out of compliance for disinfection composition, the stored or collected potable water can be treated in that location or, if necessary, diverted so that the out-of-compliance water is not delivered to the consumer. In some non-limiting embodiments, the water is sampled at or near a water storage tank or water storage location that is downstream from the water treatment facility. Water can also be manually or automatically sampled from a well source.

The relevance of free ammonia to disinfectant composition in water systems where secondary disinfection includes chloramination has increased the availability of free ammonia sensors in recent years. Notably, existing free ammonia estimate techniques require the use of additional reagents. The use of reagents that must be stored, measured, and re-supplied greatly increases the complexity of free ammonia measurements. Thus, the ability to easily estimate the amount of free ammonia in a water sample derived from a municipal water supply, as in the present invention, provides significant benefits. In some non-limiting embodiments, the methodology of the present invention is substantially free of a reagent besides chlorine and ammonia-containing materials because ORP probes used, according to the description herein, use an electrical circuit to generate the measurements. The substantial absence of reagents needed to generate free ammonia estimation using the present invention is a marked improvement over existing methodologies. Still further, free ammonia estimation, according to the present invention, does not require concurrent determination of the monochloramine concentration using colorimetric determination in order to obtain an estimation of the amount of free ammonia in real-time.

Nitrification is the two-stage biological process of converting ammonia first into nitrite and then into nitrate. Nitrification can occur in potable water systems containing natural ammonia, in chloraminated systems where free ammonia exists in excess from the chloramination process, or from decomposition of the chloramines themselves. Elevated levels of nitrate can be harmful and, thus, reduction or elimination of nitrates is a desirable outcome for municipal water supply managers. Because chloraminated water disinfection necessarily gives rise to the possibility of nitrification, it is desirable to maintain the amount of free ammonia present in a potable water supply as low as possible, while still providing a small amount. A carefully controlled amount of total chlorine to total ammonia is, therefore, necessary. Moreover, even if free ammonia is absent when the water supply leaves the water treatment plant—where chemical dosing and detection methodologies can be more closely monitored and controlled—free ammonia can be released as the water travels to the customer as the disinfectant attacks bacteria or reacts with organics that generally exist in any distribution system. The released free ammonia acts as a food source for nitrifying bacteria. This can lead to nitrification and biofilm re-growth in the distribution system. The nitrification and biofilm re-growth process consumes the effectiveness of disinfectants and can lead to corrosion in the distribution system. Beyond the health and regulatory issues, customer taste and odor complaints can result directly from nitrification or from free chlorine reversions used to treat the issue. If uncontrolled, costly and disruptive line flushes may be required. In this regard, it is beneficial to be able to accurately and easily estimate free ammonia levels after the water leaves the treatment plant.

In certain non-limiting embodiments, therefore, the present invention also comprises methods and devices for detecting the presence and relative amounts of free ammonia in a water sample derived from a water supply of interest. The present invention also provides methods and devices to reduce nitrification risk of water in municipal water supplies. Yet further, the present invention provides a nitrification risk factor that allows municipal water supply operators to assess whether nitrification is likely to happen in their system.

The present invention allows a substantially direct estimation of the free ammonia species present in a water sample, so as to substantially eliminate the need to overshoot the monochloramine part of the curve to generate knowledge of whether and how much free ammonia was present in the water sample before addition of the chlorine (or chlorine containing species). Such ability to directly estimate free ammonia present in potable water provides a significant advance over existing methodologies to inline treat water supplies in secondary disinfection regimes.

In particular, the present invention allows inline direct estimation of the free ammonia content of a water supply in situ by use of ORP dose response curves generated for a plurality of free ammonia concentrations, monochloramine, di- and tri-chloramine concentrations, pHs, and temperatures of relevance in water supplies, including but not limited to municipal water supplies and well water. The various dose response curves can then be used in an inline process whereby a water sample is automatically pulled from the water supply and chlorine (or a chlorine-containing material) is titrated therewith in the presence of an ORP electrode. The resulting ORP electrode response upon addition of the chlorine-containing material is then compared to the corresponding ORP dose response curve, so as to provide an estimation of the amount of free ammonia present in the water supply.

In some non-limiting embodiments, the present invention allows a water supply operator to detect the real-time condition of a water supply in relation to the amount of free ammonia present. This, in turn, provides an improvement in the ability to substantially maintain the amount of free ammonia in a water supply to the optimum range of greater than 0 mg/L to about 0.1 mg/L.

In particular, free ammonia in chloraminated systems cannot readily be determined by traditional total ammonia methods. Traditional colorimetric methods for ammonia such as the phenate, salicylate, and the other methods, suffer to various degrees from interference due to monochloramine, dichloramine, or organic chloramines. The level of interference in these methods depends on the chloramine concentration, the form of the organic chloramines present and the unique characteristics of the method being used. This means that chloramine level must also be determined so that the value can be subtracted out of the free ammonia detection results.

Should the real time ORP measurements indicate that the amount of free ammonia present is above the desired range, chlorine (or chlorine-containing materials) can be added using known methods. If the chlorine residual concentration needs to be increased or "boosted" to maintain a safe disinfectant level throughout the remainder of the distribution system, chlorine can be added. Either of these additions can be done at elevated water tanks, storage reservoirs, entrances to consecutive systems, or at selected points in low residual or troublesome sections in a distribution system. Feeding chlorine (or chlorine-containing material) and ammonia (or ammonia-containing material) in the specified ratio forms additional chloramines, thereby providing the necessary secondary disinfection to ensure safe and good tasting water for consumers. Such feeding can be conducted using automatic methods that provide inline treatment.

The chlorine (or chlorine-containing material) addition levels can be determined by standard volumetric addition calculations. When the water is present in a storage container, such as a water tank, the calculations are conducted to apply the chlorine (or chlorine-containing material) in batch form. When the chlorine (or chlorine-containing material) is added to a water pipe while the water is flowing therein, process control addition processes can be used. For example, a pipe with 1000 liters per minute of flow would need 1 g/min of chlorine addition to achieve a residual disinfectant raise of 1 mg/l.

Alternatively, should the real time ORP measurements indicate that free ammonia is not detectable, it will then be apparent that the chlorination disinfection regime has moved from monochloramine to di- or trichloramine region, or even past the chlorine breakpoint region.

To generate an ORP measurement of the water sample, from which the disinfectant composition of the potable water supply can be determined, the water sample to be tested is placed in the presence of an ORP sensor, such as an ORP electrode. The oxidant, that is, the chlorine (or chlorine-containing material) is added to the water sample, where the oxidant has a known concentration. The ORP measurement device provides a response that is measured in millivolts, and it is this dose response relationship that is plotted to generate data from which the chemical materials of interest and amounts thereof can be derived.

Testing of water supply using ORP involves, for example, introducing an oxidant into the sample in a known volume and following the change in electro-chemical potential resulting from the oxidant addition. The ORP measurement apparatus will follow the electrochemical potential signal generated from the oxidant addition. In regard to chlorine as the oxidant, the stoichiometry of the chloramine reaction states that one part of chlorine reacts with one-part ammonia on a molar basis (or 5:1 ratio on a weight basis).

ORP electrodes and attendant reporting componentry are available from a wide variety of suppliers, for example, Myron L Company's 720 Series of measurement devices.

Moreover, unlike with other ORP methodologies, the robust methodology herein substantially does not require ORP electrodes to be precisely maintained to ensure that results provide accurate estimations of disinfectant composition of a municipal water supply. In this regard, baseline ORP measurements can be taken as the treated water (that is, water that has undergone primary disinfection) leaves the treatment facility. ORP measurements can be taken at one or more locations in the water distribution network (that is, at a water storage tank, etc.), and those results compared to the results at the water treatment plant to obtain an estimation of whether the water sample, and, therefore, the water supply that is evaluated downstream from the water treatment facility maintains suitable disinfection efficacy. In short, the pH, temperature, and dissolved salt content of the water will not change markedly from the point that the water leaves the treatment plant until it reaches the consumer. Indeed, if these characteristics of the water did change, the water system could be experiencing significant failure that would go beyond the need to estimate disinfectant composition. Thus, the inventors have found that reliable ORP measurements can be obtained within a single water system as described herein.

While ORP electrodes may generate buildup of residue and/or memory effects over time, those effects will be gradual. Therefore, comparison of results from hour to hour or day to day or week to week or even month to month have been found by the inventors to be fairly reliable. Moreover, any measurements that are affected by changes in the ORP electrodes over time can also be measured and disinfectant composition estimations adjusted in relation thereto. This means that the ORP measurement device can either remain in the field for use and/or be deployed for an extended time period within a municipal water system distribution network substantially without maintenance.

The inventors herein have further determined, in some non-limiting embodiments, that valuable information about the disinfectant composition of a water supply that is downstream from a water treatment facility can be obtained by estimating the presence (or absence) of chemicals relevant to disinfection, as opposed to generating precise measurements of such chemicals. Notably, potable water analysis has traditionally been directed toward finding the actual chemical makeup, including amounts, in order to comply with regulatory requirements, as well as to provide safe water to consumers. The inventors herein have identified a way to ensure that water that is compliant and safe in relation to sanitization level when it leaves the water treatment facility and remains so as it travels through the water distribution network on its way to the consumer, namely by using ORP to estimate the disinfection level of the potable water. Such estimation provides "good enough" information about disinfectant composition, and the simplicity of the methodology herein relative to other methods of measurement used historically, enables cost effective real time measurement of disinfectant composition. Moreover, the use of ORP is highly suitable for estimation of the disinfectant composition of chloraminated systems as described in detail herein.

In certain non-limiting embodiments, the present invention is used to measure chloramination levels and/or free ammonia levels of potable water, that is water intended for ingestion by humans. Yet further, the present invention consists essentially of measuring the chloramination levels and/or free ammonia levels of potable water. Still further, the present invention is substantially not used to measure the levels of free chlorine in potable water.

Additionally, the robust methodology herein allows comparison of results from different water supplies to be compared in an "apples to apples" framework, such that the disinfectant composition of different water treatment regimens or scenarios can be evaluated both within a single municipal water system (e.g., different locations downstream from the water treatment plant) or among different municipal water systems (e.g., different cities in a regulatory jurisdiction). Widespread deployment of ORP to estimate disinfectant composition of a water system may serve to improve the evaluation of potable water quality generally. Such improvements are enhanced by use of the inventive ORP methodology in water systems as discussed in more detail hereinafter.

Referring to FIG. 1, addition of chlorine (or other oxidants) to the water sample results in a change in millivolts, as measured by a properly configured ORP electrode. In FIG. 1, the chlorine addition regime is presented in relation to evaluating and, in some non-limiting embodiments, adjusting the chloramination and/or free ammonia levels of potable water. In the section denoted "A", addition of chlorine will be in the form of salt formation and combination of chlorine with organic materials in the water. As such, the section denoted "A" will provide substantially no disinfection efficacy because the chlorine is not available to provide disinfecting activity. Practically speaking, in a secondary disinfection regime, at least some chlorine should be present in the water sample because of an addition in the water treatment plant, that is, in the primary disinfection regime. Accordingly, ORP measurements in the present invention will be with reference to points later in the plot after "A."

In accordance with a desired secondary disinfection regime, detection of free ammonia in relation to generation of a suitable disinfection activity with no foul tasting di- and trichloramine formation will be relevant primarily in the point just to the left of the point marked "X." This can be termed as the "sweet spot" for chloraminated disinfection systems, that is, where the optimum stoichiometry of chlorine to ammonia of substantially equal to 1:1 molar ratio is obtained. At this point, there will be substantially no free ammonia present—and, thus, substantially no nitrification potential—and substantially all monochloramine species will exist as the chloramination disinfecting species. When a threshold level of additional chlorine containing material is added, the dichloramine and, at higher chlorine concentrations, trichloramines (collectively denoted "C") will become the predominant chloraminated species. While these materials have some disinfecting capabilities, they are sour smelling and tasting, and, thus, signal to consumers that their potable water is not high quality. Free ammonia will be absent to the right of the section denoted "B."

Moreover, since monochloramine requires significantly less chlorine to generate, the presence of di- and trichloramines signify that the water system operators are using more chlorine than necessary to achieve disinfection composition. Thus, the present invention also suitably allows water system operators to manage the amount of chlorine they are using in secondary disinfection regimes. When the amount of chlorine reaches the "breakpoint," that is, where the chlorine is no longer combined with ammonia, chlorine will be present in the water sample substantially as free chlorine, $Cl_2$ (denoted as "D"). As would be recognized, free chlorine is largely undesirable in modern water treatment systems because of the propensity of undesirable chlorinated compounds to be developed. Moreover, the presence of free chlorine in a secondary disinfection regime also signifies that a great excess of chlorine is present in the water supply. Again, the ability to readily detect the presence of chlorine in a water sample extracted from a water supply using ORP greatly simplifies management of chlorine addition and use in secondary disinfection regimes.

In accordance with the detection regime of the present invention, the disinfectant composition represented by monochloramine present in the water sample, and, thus, in the water supply at the point where the water sample is taken, can be determined by evaluating the slope of the curve generated by plotting the relationship—that is, the dose response—between added chlorine and ORP measurement, as presented in millivolts. The change from monochloramine to dichloramine will be apparent when there is a change in the slope of the curve, as denoted by "X" on FIG. 1. At that point, the added chlorine will combine with the monochloramine to create di- and trichloramines Thus, measured chlorine residual will decrease, and the ORP measurement will change because the redox reaction is changing. It is this change that allows determination of the disinfectant composition of the water sample, and, thus, the water supply at the location from which it was extracted.

The free ammonia level can also be generated from the ORP curves generated for a water sample. The point just before this slope change at X will comprise only a small amount of ammonia (more than 0 mg/L) and less than about 0.1 mg/L.

Moreover, the pH, temperature, and dissolved salts are unlikely to change markedly from hour to hour or day to day or week to week within the same municipal water supply. Thus, any pH, temperature and dissolved salt effects between and among measurements are likely to be very small, or at least small enough to not substantially reduce the accuracy of the measurements within the time scales relevant to ensuring disinfectant composition of a municipal water supply. Notably, the recognition that pH, temperature, and dissolved salt effects, while highly influential to laboratory use of ORP, do not practically affect the viability of ORP in evaluating municipal water supplies or in well water in real time, or substantially in real time, represents a marked improvement in potable water quality evaluation. In the present invention, pH and temperature can be measured concurrently with an ORP measurement, however, such pH and temperature measurements are typically used to confirm that the water sample has consistent qualities to a first water sample obtained from the same water source. For example, if a pH measurement of a first water sample is 7.1, but the subsequent water sample taken from the same water source is 8.5, then it may be indicated that some type of contamination occurred in the water source as it traveled through the water distribution system. Wide variations in pH and temperature can also affect the estimation values, and are relevant to measure. Nonetheless, in most real use circumstances the pH and temperatures of the water supply will not vary substantially between water sample measurements.

In further non-limiting embodiments, the present invention provides methodologies to estimate the level of residual chlorine-containing material, in the water sample, and, therefore, the water supply from which it is derived, where residual chlorine-containing material comprises monochloramine, dichloramine, trichloramine, and, in some cases, free chlorine. The chemical identities of these materials are provided by evaluating slope changes in the curve resulting from plotting the relationship between added chlorine and ORP measurements.

While the ORP methodology disclosed herein provides benefits when used independently, further utility is found when the invention is incorporated in an overall water monitoring and treatment system, such as would be relevant with a municipal water supply system or a well. In this regard, the improved chloramination and free ammonia measurement system allows substantially real-time measurement of chloramination levels to enable water system operators to better ensure that water is not just safe and compliant when it is initially treated in a water treatment facility, but that it remains safe and compliant when it is delivered to consumers. Yet further, the system herein can allow baseline free ammonia levels to be determined in well water, and provide disinfection thereof. Whether used on municipal water supplies or on well water, the methodology herein substantially reduces the likelihood that nitrification of previously chloraminated water will occur, enabling improved measurement and control of free ammonia levels in water. In sum, the various aspects of the present invention allow water system operators to set and maintain consistent disinfectant levels in water supplies, as well as allowing them to substantially eliminate costly and labor intensive manual disinfectant testing and adjusting.

In certain non-limiting embodiments, the present invention allows water system operators to monitor and, therefore, treat and maintain, water quality substantially without an attendant monitoring the concentrations of the feed source, namely chlorine and ammonia. This allows the chlorine and ammonia to be stored in high concentrations for extended periods substantially without an attendant monitoring the concentration of the material. Operators are able to add chlorine or ammonia to a water supply, for example, a water tank, and to determine the appropriate additional level of chlorine or ammonia by examining the ORP dose response readings. In this regard, the present invention further comprises a system to treat a water supply comprising adding one or more of chlorine and ammonia to the water supply and measuring the ORP behavior using an ORP electrode, where the additional levels are directed by observing the ORP electrode behavior.

In this regard, the ORP dose response curve of FIG. 1 can be used to define the addition of chlorine or ammonia to the water supply. Notably, the ORP behavior of the water sample will allow the operator to know the effective disinfectant level of the water supply. Addition of a chlorine or ammonia source to that sample will be in relation to the known dose response behavior that is substantially independent of the concentration of the chlorine or ammonia being added. To provide appropriate adjustment of the water supply, the operator need only know the approximate volume of the water supply to which the multiple of the chlorine or ammonia needs to be applied to generate approximately the same dose response for the water supply. For example, a chlorine feed source added to a water sample of 1 L provides a dose response that indicates that 0.5 ml of chlorine needs to be added to generate an appropriate level of monochloramination, and the total volume of water in the water supply, such as in a water tank, is 500,000 L, the operator can add 0.5 ml*500,000 L=2.5 L of chlorine to the water supply to obtain the desired level of disinfectant. This aspect of the present invention presents a substantial improvement over prior art methods that require precise dosing of a known concentration of chlorine to achieve an appropriate level of disinfection of a water supply.

Figure 2:
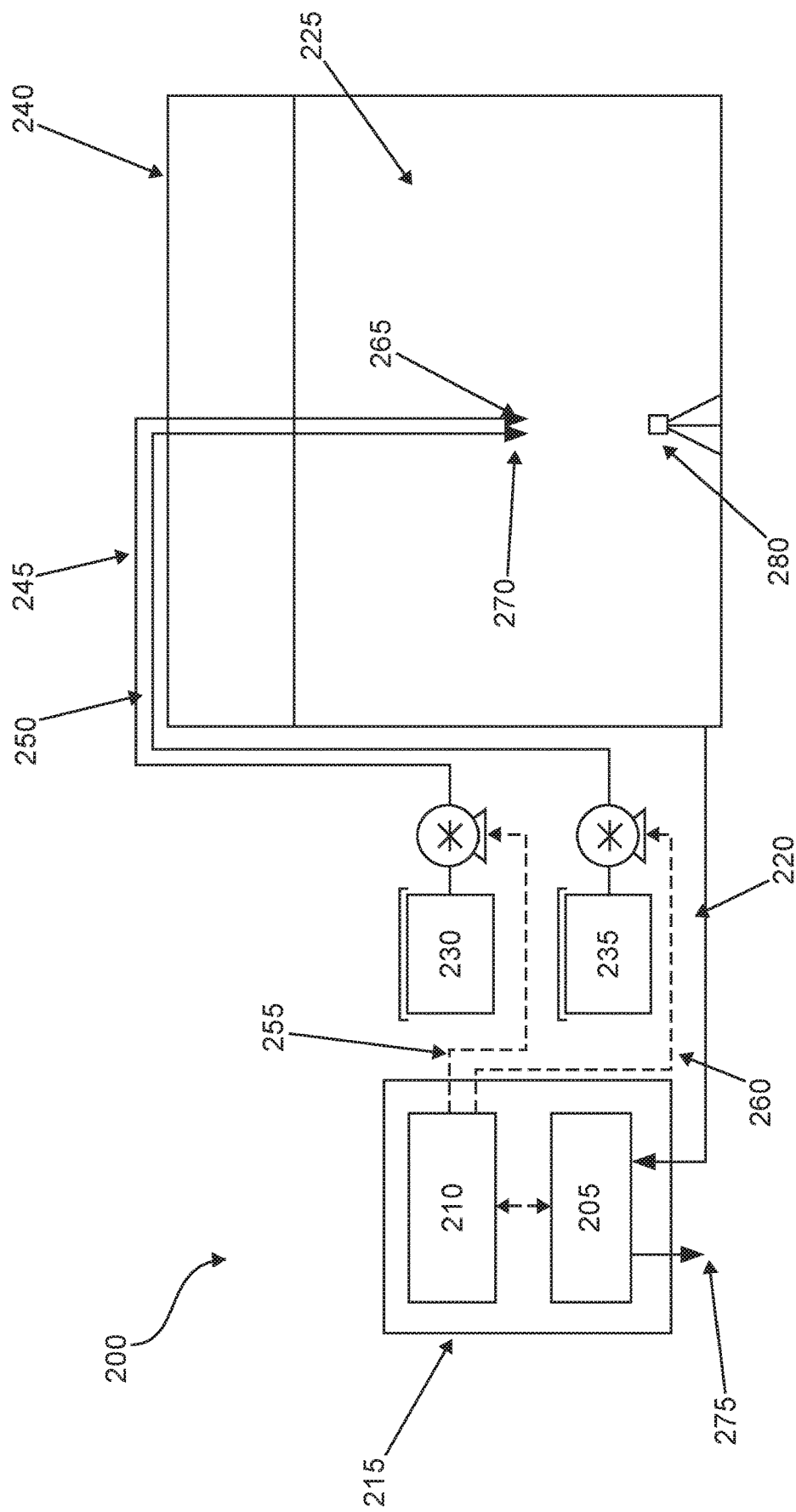
FIG. 2 illustrates an exemplary system in which the inventive methodology can be implemented.

Referring to FIG. 2, an exemplary configuration of a disinfectant management system 200 in accordance with an implementation of the present invention is illustrated therein. System 200 comprises various aspects, including a plurality of sensors 205 configured to generate at least ORP measurements. Other sensors 205 that can be used with the system 200 include sensors to generate pH measurements and/or temperature measurements. Additional sensors can be included in the plurality of sensors 205, where such additional sensors can be configured to provide measurements of free chlorine, total chlorine, and the like.

System 200 also includes control module 210 configured with software and hardware. The combination of the plurality of sensors 205 and control module 210 provides a water quality assessment module 215.

As would be understood, the plurality of sensors 205 are in operational communication with the hardware and software aspects of control module 210. In use, water quality assessment module 215 allows a water system operator to monitor, control, and generate data about a water system under management as a substantially integrated system.

Water quality assessment module 215 can be operated on a wide variety of hardware devices including, but not limited to, PCs, tablets, mobile devices, etc. Software operations, which will include various algorithms associated with system 200 and the various components therein configured with use therein, can be maintained in the cloud on a remote server, or they can be operated using software that is natively installed on or used in conjunction with system 200. As such, suitable microprocessor and computer controls are incorporated into system 200 herein to enable operation of system 200 in accordance with the inventive methodology herein. In further non-limiting embodiments, system 200 can be configured to transmit real time data to water system managers and/or technicians who may be remote from system 200 via cellular, Wifi, Bluetooth® communication, or the like.

The integration of the various aspects associated with maintaining water quality in accordance with the invention herein allows operators to program the various parameters associated with maintaining a suitable disinfection level/ composition of chloraminated water supplies, free ammonia determination in water supplies, and, optionally, other water quality characteristics. Still further, the integration of the various aspects herein allows an operator to continuously or periodically monitor and treat water quality data generated from water quality assessment module 215.

In use, a water sample (not shown) is collected via a sample line 220 from water supply 225, which is in a water tank 240 in FIG. 2. Sample line 220 is operationally engaged with a pump (not shown) and water sample delivery means (not shown), for example, a pipe or tube or hose to direct the water sample to the plurality of sensors 205, which in pertinent part includes at least an ORP sensor (not shown) and, optionally, a pH sensor (not shown) and a temperature sensor (not shown). Water quality assessment module 215 is configurable to activate the pump (not shown) so as to provide a suitable volume of water sampled from water supply 225. If the water sample is found to have a disinfectant level or free ammonia level outside of a desired set point, control module 210 will provide instructions to at least one of chlorine feed source 230 or ammonia feed source 235 to add suitable material so as to maintain uniform and consistent water quality within water supply 225. While system 200 can be utilized in any municipal water supply configuration, FIG. 2 illustrates a water supply 225 contained in a water storage tank 240.

As shown in FIG. 2, chlorine feed source 230 and ammonia feed source 235 are in fluid communication with water supply 225 contained in water tank 240 via chlorine injection line 245 and ammonia injection line 250, respectively. Chlorine feed source 230 and ammonia feed source 235 are in operational communication with the respective injection lines 240 and 245 as shown by 255 and 260, respectively. Further, as shown in FIG. 2, chlorine injection line 245 and ammonia injection line 250 each terminate in chlorine injection nozzle 265 and ammonia injection nozzle 270, respectively. Alternatively, chlorine injection line 245 and ammonia injection line 250 can be joined via a connection point (not shown) and the respective chemical injection can be provided by a single chemical injection nozzle (not shown).

In use, the water quality assessment module 215 can be configured to monitor disinfectant level of water supply 225 via periodic or substantially continuous collection of a plurality of water samples (not shown) via sample line 220, where at least a portion of each water sample is provided to one or more of the sensors (not shown) of the plurality of sensors 205. In some non-limiting embodiments, each water sample is evaluated by each of the sensors in plurality of sensors 205 in each water sampling event. Yet further, only some of the sensors in plurality of sensors 205 are used in each water sampling event. For example, the disinfectant level related sensors in plurality of sensors 205, namely ORP, pH, and temperature sensors (not shown) can be used on an ongoing basis (that is, substantially continuously or periodically), and other sensors included in plurality of sensors 205 can be used less frequently.

A notable improvement in system 200 over prior art systems is that real time or substantially real-time information about the disinfectant composition of water supply 225 can be provided, or historical data can be generated, maintained, and evaluated. In addition, water quality data from other sources, such as manual samples, can be inputted into the system to provide a comparison and archive of multiple measurement methods. This allows water system operators and managers to collect data on the quality of the water within the system 200 for any duration of time from minutes to years. Such data allows water system operators to evaluate day to day operations, react to unexpected changes in water chemistry, and observe the effects of treatment plant changes on distribution system water quality.

In particular, chlorine feed source 230 and ammonia feed source 235 are each independently configured to inject disinfectant materials into water supply 225. As noted, control module 210 provides instructions for addition of chlorine and/or ammonia via operational communication 260 and 265, which can be wired or wireless. Water quality assessment module 215 is accordingly configured to monitor the system via the plurality of sensors 205 so as to provide pertinent information regarding at least the disinfectant level of water supply 225 in system 200, including providing alarms or other signals to an operator, if needed. In this regard, system 200 is configured to alert the user of any irregularities within the system and produce an automated response, from an alert on the screen to system shut down, in order to ensure safe operating conditions. System 200 further incorporates a drain 275 in operational communication with water quality assessment module to allow removal of the water sample after testing thereof.

When the water supply 225 in need of monitoring is incorporated in a water tank 240, as shown in FIG. 2, an active mixing module 280 can be included. Such an active mixing module 260 can comprise, but is not limited to, a submersible mixing system that is usable for use in storage tanks (as shown in FIG. 2) and reservoirs (not shown). Optimally, active mixing module 260 will rapidly and completely mix the disinfectant chemicals inserted via chemical feed nozzle 250 and/or ammonia feed nozzle 255 into the entire volume of water supply 225 in tank 230 or reservoir (not shown) or well (not shown), enabling rapid homogenization and maximum water quality stability and reliability. The methodologies and devices disclosed in U.S. Pat. Nos. 5,934,877, 6,702,552, 7,488,151, 7,862,302, and 9,039,902, which are incorporated by reference herein in their entireties, are suitable for use in some mixing aspects of the invention.

A number of embodiments have been described but a person of skill understands that still other embodiments are encompassed by this disclosure. It will be appreciated by those skilled in the art that changes could be made to the embodiments described above without departing from the broad inventive concepts thereof. It is understood, therefore, that this disclosure and the inventive concepts are not limited to the particular embodiments disclosed, but are intended to cover modifications within the spirit and scope of the inventive concepts including as defined in the appended claims. Accordingly, the foregoing description of various embodiments does not necessarily imply exclusion. For example, "some" embodiments or "other" embodiments may include all or part of "some", "other," "further," and "certain" embodiments within the scope of this invention.

The invention claimed is:

1. A method of determining a disinfectant composition of a municipal water supply from a water sample comprising:
   a. obtaining a water sample from a water source at a sampling location, wherein:
      i. the water sample is derived from a water treatment facility;
      ii. a chlorine-containing material and an ammonia containing material are present in the water source; and
      iii. the sampling location is located downstream from the water treatment facility;

b. adding an additional chlorine-containing material to the water sample in the presence of an oxidation reduction potential (ORP) measurement device;

c. generating a plurality of ORP measurements during addition of the additional chlorine-containing material to the water sample;

d. estimating a concentration of one or more of free ammonia, fully combined ammonia, monochloramine or a mixture of dichloramine and trichloramine in the water sample, wherein the estimation is derived from the relationship between the added additional chlorine-containing material and the plurality of ORP measurements; and e. determining a disinfectant composition of the water source at the water sampling location based upon the concentration estimation, wherein determining the disinfectant composition in step e comprises determining a free ammonia composition of the water supply and wherein at least a concentration of free ammonia in the water sample is estimated in step d.

2. The method of claim 1, wherein the concentration is estimated from monitoring the rate of change of ORP measurement in millivolts as a function of the amount of additional chlorine-containing material added to the water sample.

3. The method of claim 1, wherein the concentration is estimated by calculating a slope obtained by plotting the plurality of ORP measurements of the water sample versus the amount of additional chlorine-containing material added to the water sample.

4. The method of claim 1, wherein the disinfectant composition is determined as a real-time measurement.

5. The method of claim 1, wherein the additional chlorine-containing material is added to the water sample in a known volume while generating the plurality of ORP measurements to determine the relationship between the added additional chlorine-containing material and the plurality of ORP measurements.

6. The method of claim 1, further comprising comparing the plurality of ORP measurements obtained from the water sample located downstream from the water treatment facility to ORP measurements obtained from a water sample obtained at the water treatment facility to determine disinfection efficacy.

7. The method of claim 1, wherein the estimation provides the concentration of both free ammonia and monochloramine in the water sample.

8. The method of claim 1, further comprising, after determining the disinfectant composition of the water source, adding additional chlorine-containing materials and ammonia-containing materials to the water source to achieve a desired level of the disinfectant composition.

9. The method of claim 8, wherein an amount of the added chlorine-containing materials and ammonia-containing materials is independent of a concentration of the chlorine-containing materials and ammonia-containing materials.

10. The method of claim 1, wherein a volume of the water sample obtained from the water source is known.

11. A method of determining free ammonia composition of a water supply comprising:

a. obtaining a water sample from the water supply at a sampling location;

b. adding a chlorine-containing material to the water sample in the presence of an oxidation reduction potential (ORP) measurement device;

c. generating a plurality of ORP measurements during addition of the chlorine-containing material to the water sample; and d. estimating a concentration of free ammonia in the water sample, wherein the estimation is derived from the relationship between the added chlorine-containing material and the plurality of ORP measurements.

12. The method of claim 11, wherein a volume of the water sample obtained from the water supply is known.

13. The method of claim 11, wherein the water sample is derived from a water treatment facility and the sampling location is located downstream from the water treatment facility.

14. The method of claim 11, further comprising maintaining the concentration of free ammonia in the water supply within a range of greater than 0 mg/L and less than about 0.1 mg/L.

15. The method of claim 11, wherein the method of determining free ammonia composition is substantially free of a reagent other than chlorine and ammonia-containing materials.

16. The method of claim 11, wherein the concentration of free ammonia is estimated from monitoring the rate of change of ORP measurement in millivolts as a function of the amount of chlorine-containing material added to the water sample.

17. The method of claim 11, further comprising adding additional chlorine-containing materials when the estimated free ammonia concentration is above a desired free ammonia concentration range.

* * * * *